United States Patent [19]
Schulze

[11] Patent Number: 5,421,037
[45] Date of Patent: Jun. 6, 1995

[54] COMBINED GOGGLES AND HEADBAND ASSEMBLY

[76] Inventor: Bradford L. Schulze, 1309 Girard, Indianola, Iowa 50129

[21] Appl. No.: 212,815
[22] Filed: Mar. 15, 1994
[51] Int. Cl.6 .................. A61F 9/04; A41D 21/00
[52] U.S. Cl. .................................. 2/452; 2/209; 2/909
[58] Field of Search .................. 2/452, 909, 918, 209, 2/449, 454, 426, DIG. 11, 423, 171, 209.3

[56] References Cited

U.S. PATENT DOCUMENTS

| | | |
|---|---|---|
| D. 33,250 | 11/1992 | Acosta et al. . |
| 4,682,374 | 7/1987 | Geiser ..................................... 2/209 |
| 4,751,746 | 6/1988 | Rustin .................................. 2/209 X |
| 4,849,863 | 7/1989 | Gallegos ............................. 2/909 X |
| 5,038,412 | 8/1991 | Cionni . |
| 5,092,667 | 3/1992 | Bagley . |
| 5,153,939 | 10/1992 | Howe et al. . |
| 5,201,856 | 4/1993 | Edwards ................................. 2/209 |
| 5,231,704 | 8/1993 | Hildenbrand ....................... 2/209 X |
| 5,257,420 | 11/1993 | Byrne, Jr. ............................... 2/209 |

Primary Examiner—Peter Nerbun
Attorney, Agent, or Firm—Henderson & Sturm

[57] ABSTRACT

A combined goggles and headband assembly comprising a goggles unit including a unitary goggles connected by a retaining strap for encircling the head of a wearer, and a cover for the ears of the wearer comprising a piece of cloth and fasteners of a length and width to encircle the retaining strap from opposed end edges of the goggles.

1 Claim, 2 Drawing Sheets

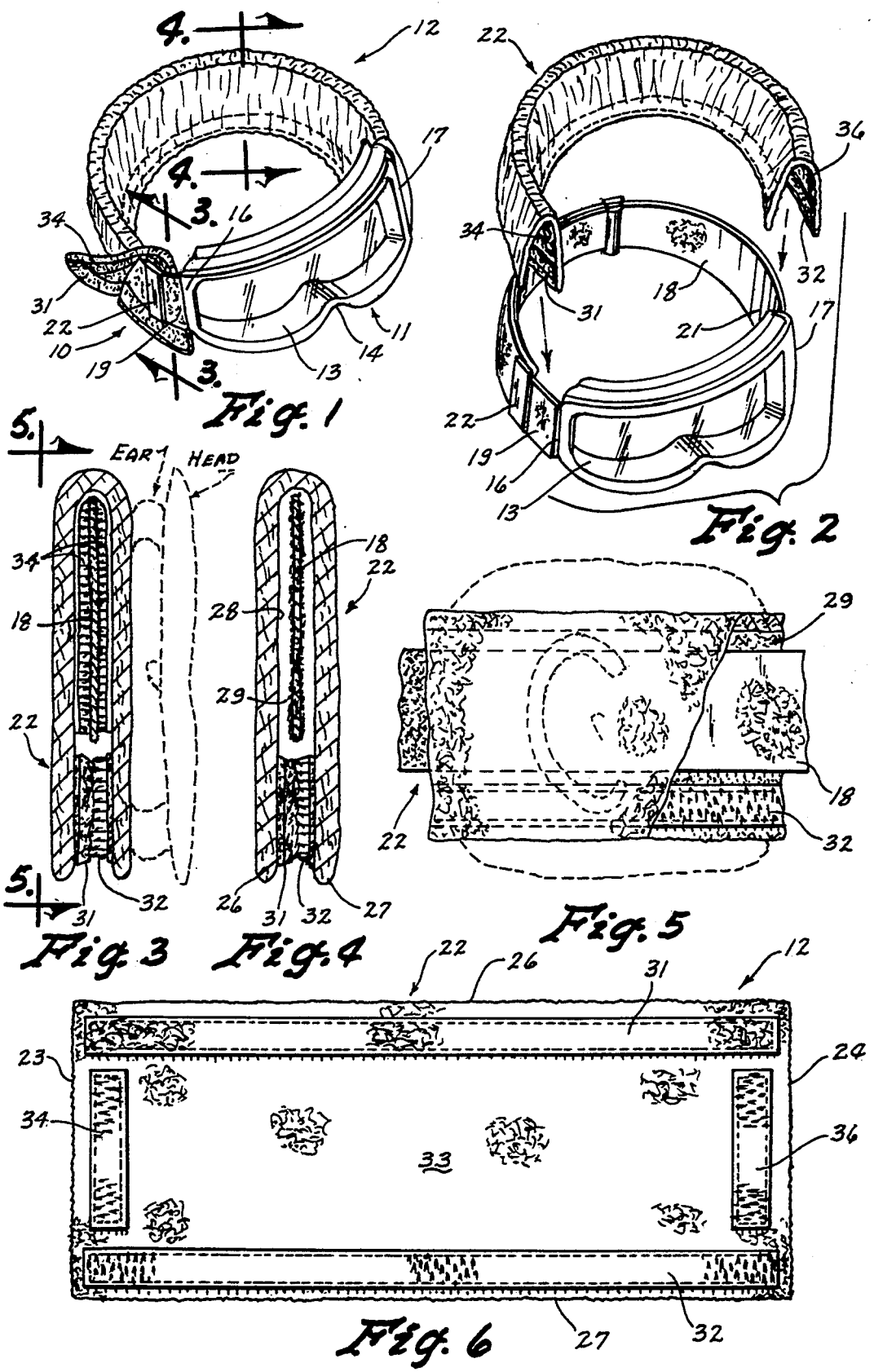

COMBINED GOGGLES AND HEADBAND ASSEMBLY

TECHNICAL FIELD

The invention relates to a combined goggles unit and a cloth unit for cooperative fastening to the goggles unit for covering both the eyes and ears of a wearer for protective purposes.

BACKGROUND OF THE INVENTION

Goggles are of course well known to the prior art, and are widely available to the consumer at numerous commercial outlets. Contemporary goggles are provided, in some instances in specialty form, for bicycling, both snow and water skiing, diving—both water and air, and all forms of contact sports for the provision of both and/or enhancing the sight of the wearer and of protecting the eyes.

Headbands are also widely known for a variety of purposes: keeping the perspiration out of a wearer's eyes; keeping hair out of a wearer's eyes; use in the form of earmuffs to keep a wearer's ears warm—both as a participant, i.e., winter sports, running; and lastly but certainly not least, as ornamental clothing.

DISCLOSURE OF THE INVENTION

The present invention combines a goggles unit, including an integral, unitary goggles and an adjustable retaining strap for encircling a wearer's head and for covering a wearer's eyes, and providing a blank piece of cloth sized to completely encircle the retaining strap from opposed side edges of the goggles, and to cover the wearer's ears at the same time, cooperative fastening strips being secured to appropriate portions of the cloth piece to provide for releasable securement thereof to the retaining strap.

In one embodiment, the cloth blank is of a rectangular shape with cooperative fasteners being secured on one face thereof, such that upon a doubling over of the cloth blank, the edges are connected to each other, forming and leaving a longitudinal passage interior therein to receive and embrace the retaining strap.

In another embodiment the opposed longer side edges are laterally extended in an outwardly curved manner such that upon the cloth blank being folded longitudinally upon itself, the mating extended side edges form more of an "earmuff" appearance and function.

Other feathers and advantages of the invention will be apparent from the following description of a preferred embodiment, including illustrations and appended claims.

BRIEF DESCRIPTION OF THE DRAWINGS

FIG. 1 is a perspective view of one embodiment of the combined goggles and headband assembly of the present invention;

FIG. 2 is an exploded view of FIG. 1, showing the goggles unit and headband unit;

FIG. 3 is an enlarged sectional view as taken along the line 3—3 of FIG. 1;

FIG. 4 is another sectional view as taken along the line 4—4 of FIG. 1;

FIG. 5 is a reduced elevational view as taken along the line 5-5 in FIG. 3;

FIG. 6 is a plan view of one face of the blank piece of cloth of the headband unit and showing the placement of cooperative fastening strips;

BEST MODE FOR CARRYING OUT THE INVENTION

Figure 7:
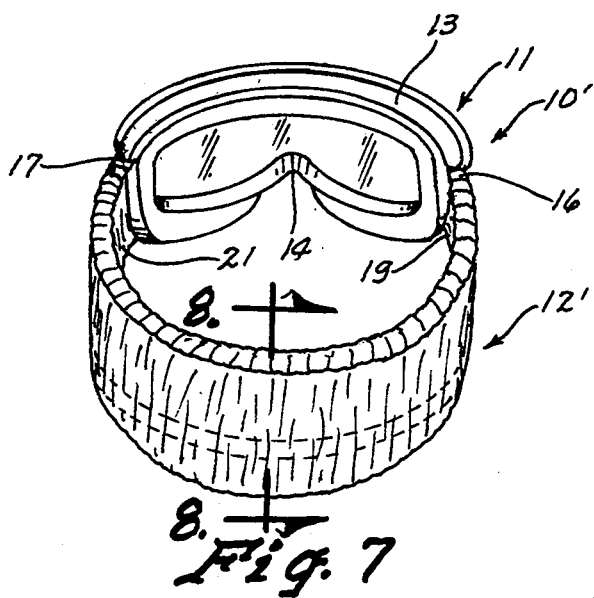
FIG. 7 is a perspective view similar to FIG. 1 of an alternate embodiment of the invention.

Referring now particularly to FIGS. 1–6, wherein like parts are referred to with like reference numerals, the combined goggles and headband, assembly of this invention is referred to generally at (10), and includes a goggles unit (11) and a headband unit (12).

The goggles unit (11) comprises an integral, unitary goggles (13) for covering the eyes of a wearer, with an appropriate indentation (14) for the nose, there being end loops (16), (17) for receiving an adjustable strap (18). The strap (18) of an appropriate, flexible cloth material, has opposite ends (19), (21) adapted, one end (19) for example, using a buckle (22) for adjustment purposes to be releasably connected to the goggles (13) opposite end loops (16), (17). The strap (18) is adjusted to a length adapted to encircle a wearer's head so as to hold the goggles (13) securely over the wearer's eyes.

The headband unit (12) comprises a rectangular one piece (FIG. 6) blank of cloth (22) having opposite end edges (23), (24) and opposite side edges (26), (27). The cloth blank (22) is preferably fabricated of a relatively warm fabric such as 100% knitted acrylic fabric. Further, of course the fabric may be wool, cotton or blends thereof, including acrylic in the blends. The length of the cloth blank (22) between the end edges (23), (24), is sized to be substantially the same length as that of the retaining strap (18) between its connected ends (19), (21). The width of the cloth blank (22) between its side edges (26), (27) is sufficient such that upon the blank (22) folded or doubled upon itself along its longitudinal axis (FIG. 2), the resulting width, one-half the original width, is sufficient to form a loop (28) having a longitudinal passage (29) to embrace the width of the retaining strap (18) (FIGS. 3, 4) with the side edges (26), (27) placed opposite each other.

To ensure securement of the cloth blank (22) in its loop (28) condition, cooperable securing strips (31), (32) of Velcro are secured to one face (33) of the blank (22) (FIG. 6) adjacent the side edges (26), (27) thereof, and identical hook fastener Velcro strips (34), (36) are secured to the blank face (38) adjacent the end edges (26), (24). Thus, upon the blank (22) being folded, for example in the position of FIG. 2, then placed over the retaining strap (18) between the connected ends (19), (21), the end edge strips (33), (34) engage (FIG. 3) opposite sides of the strap (18); and as the strap (18) is cloth, the Velcro hook fastener strips (34), (36), engage and stick to the doth strap (18) at each strap end (19), (21). Further, the side edge strips (31), (32) cooperatively engage each other (FIGS. 3, 4) substantially the entire length of the strap (18) so as to secure the loop (28) about the strap (18). Additionally, the width of the folded blank (22) is sufficient to cover the ears (FIG. 5) of the wearer of the assembly (10), thus completing the objectives thereof.

Figure 8:
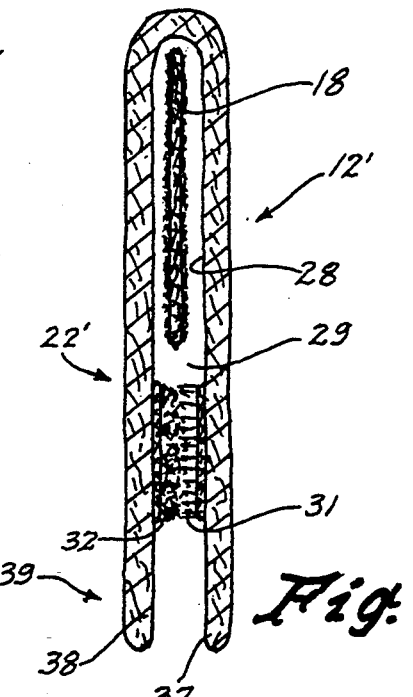
FIG. 8 is an enlarged sectional view taken along the line 8—8 in FIG. 7.
Figure 9:
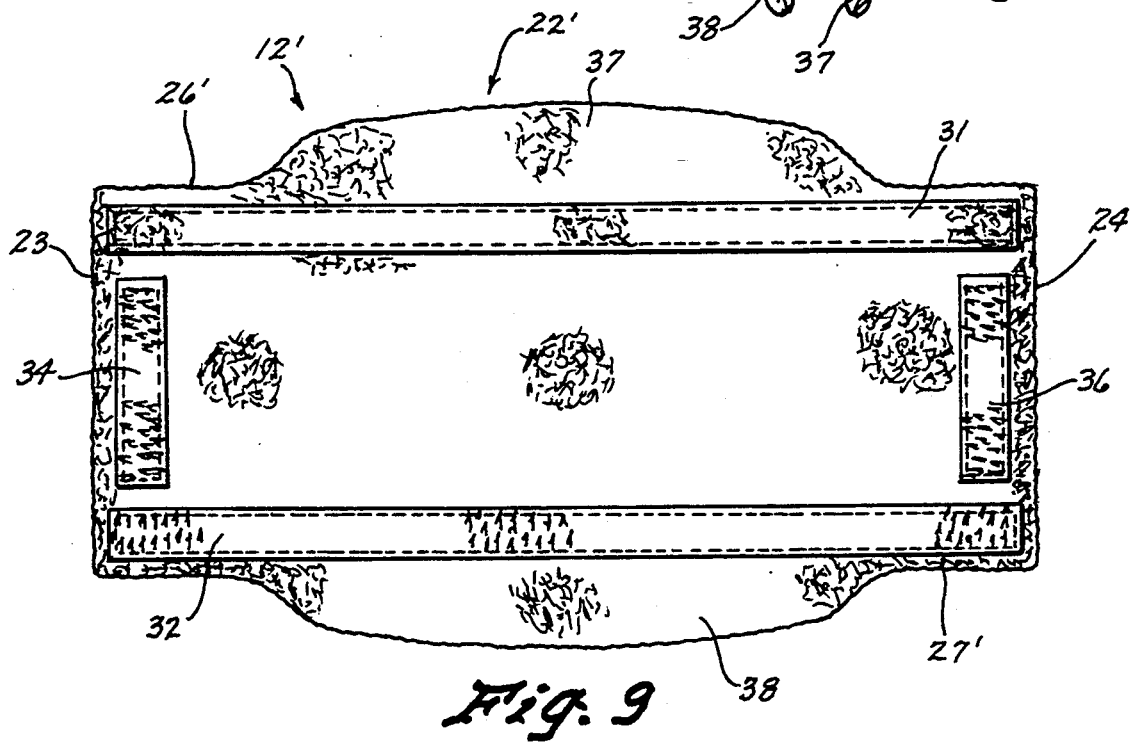
FIG. 9 is a view similar to that of FIG. 6 of one face of the blank piece of cloth of the alternate headband unit.

Referring now to FIGS. 7-9, wherein like parts to the embodiment of FIGS. 1-6 are identified by like reference numerals, the alternative embodiment shows a goggles unit (11) and a headband unit (12'). The unit (12') is different from the unit (12) of the FIGS. 1-6 embodiment only in the one piece blank of cloth (22') having portions (37) and (38) of the side edges (26'), (27') extended laterally outwardly in a concave manner intermediate the end edges (23), (24), thus widening the intermediate portion (39) of the headband blank (22').

Thus, upon folding the blank (22') longitudinally as indicated in FIG. 8 and securing it over the cloth retaining strap (18), the resultant goggles and headband assembly (10') is the same as the assembly (10) (FIGS. 3 and 4) with the exception that the intermediate portion (39) forms more of an earmuff over the wearer's ears, due to its increased width of the headband blank (22') at the ear area of the wearer).

Whereas the invention is here illustrated and described with reference to an embodiment and an alternative thereof presently contemplated as the best mode of carrying out the present invention, it is to be understood that various changes may be made thereto without departing from the scope of the invention as defined in the appended claims.

I claim:

1. A combined goggles and headband assembly comprising in combination:

a goggles unit including a unitary goggles having opposed end edges for placement over a wearer's eyes, and a retaining strap having opposed ends connected to said opposed edges, respectively and encircling a wearer's head to retain the goggles unit over the wearer's eyes; and a headband unit encircling the retaining strap, said unit including a piece of cloth foldable to a width to cover the wearer's ears, and including fastener strips secured to opposed portions of one side of said cloth piece for cooperative releasable fastening upon folding of said cloth piece and upon contacting engagement of said fastener strips;

and further wherein said cloth piece has a length substantially only equal to the length of said retaining strap as it is connected to said goggles unit opposed end edges, said cloth piece has a general rectangular shape of a width such that upon being folded lengthwise, said cloth piece encircles said retaining strap, said cloth piece having opposed side edges and opposed end edges;

and further wherein said fastener strips comprise a first set of cooperative fastener strips secured along opposed side edges of said cloth piece, and a second set of strips is secured along opposed end edges of said cloth piece for fastening with and upon said retaining strap, and said opposed side edges include laterally extended edge portions which are coextensive upon being folded to provide extended coverage of a wearer's ears.

* * * * *